(12) United States Patent
Maurel

(10) Patent No.: US 9,592,218 B2
(45) Date of Patent: Mar. 14, 2017

(54) REVERSE MICELLE SYSTEM COMPRISING METAL IONS AND USE THEREOF

(75) Inventor: Jean-Claude Maurel, Castries (FR)

(73) Assignee: MEDESIS PHARMA, Baillargues (FR)

( * ) Notice: Subject to any disclaimer, the term of this patent is extended or adjusted under 35 U.S.C. 154(b) by 0 days.

(21) Appl. No.: 13/636,421

(22) PCT Filed: Mar. 24, 2011

(86) PCT No.: PCT/EP2011/054511
§ 371 (c)(1),
(2), (4) Date: Nov. 12, 2012

(87) PCT Pub. No.: WO2011/117333
PCT Pub. Date: Sep. 29, 2011

(65) Prior Publication Data
US 2013/0052279 A1 Feb. 28, 2013

Related U.S. Application Data

(60) Provisional application No. 61/317,024, filed on Mar. 24, 2010.

(30) Foreign Application Priority Data

Mar. 24, 2010 (EP) .................... 10305298

(51) Int. Cl.
*A61K 31/28* (2006.01)
*A61K 9/107* (2006.01)

(52) U.S. Cl.
CPC .............. *A61K 31/28* (2013.01); *A23L 33/16* (2016.08); *A23P 10/35* (2016.08); *A61K 9/1075* (2013.01); *A23V 2002/00* (2013.01)

(58) Field of Classification Search
CPC .... A61K 9/1272; A61K 9/1075; A61K 31/28; A23V 2250/1604; A23V 2250/1612; A23V 2250/1632; A23V 2250/1636; A23L 33/16
See application file for complete search history.

(56) References Cited

U.S. PATENT DOCUMENTS

| | | | |
|---|---|---|---|
| 5,662,932 A | | 9/1997 | Amselem et al. |
| 5,716,639 A | * | 2/1998 | Carlsson et al. .............. 424/450 |
| 6,040,188 A | * | 3/2000 | Holman .......................... 436/71 |
| 2009/0087477 A1 | * | 4/2009 | Maurel ......................... 424/450 |

FOREIGN PATENT DOCUMENTS

| | | |
|---|---|---|
| EP | 1652513 | 5/2006 |
| FR | 2729957 | 8/1996 |
| WO | WO 96/23811 | 8/1996 |
| WO | WO 2006/048773 | 5/2006 |
| WO | WO 2009/051837 | 4/2009 |

OTHER PUBLICATIONS

Pal et al., Food and Chemical Toxicology 42, 2004, 737-742.*
Friedrich, I. et al. "Drug release and permeation studies of nanosuspensions based on solidified reverse micellar solutions (SRMS)" *International Journal of Pharmaceutics*, 2005, pp. 167-175, vol. 305.
Friedrich, I. et al. "Characterization of solidified reverse micellar solutions (SRMS) and production development of SRMS-based nanosuspensions" *European Journal of Pharmaceutics and Biopharmaceutics*, 2003, pp. 111-119, vol. 56.
Written Opinion in International Application No. PCT/EP2011/054511, Mar. 26, 2012, pp. 1-7.
Müllertz, A. et al. "New perspectives on lipid and surfactant based drug delivery systems for oral delivery of poorly soluble drugs" *Journal of Pharmacy and Pharmacology*, 2010, pp. 1622-1636, vol. 62.

* cited by examiner

*Primary Examiner* — Kyle Purdy
(74) *Attorney, Agent, or Firm* — Arent Fox LLP

(57) ABSTRACT

The present invention relates to reverse micelle system based on sterols, acylglycerols, phospholipids or sphingolipids and metal ions. Reverse micelle system of the invention is able to cross mucosa and cellular membranes. It thus allows vectorization of metal ions to target sites. It is advantageously useful in the pharmaceutical and dietetic fields.

33 Claims, 11 Drawing Sheets

REVERSE MICELLE SYSTEM COMPRISING METAL IONS AND USE THEREOF

CROSS-REFERENCE TO RELATED APPLICATIONS

This application is the U.S. national stage application of International Patent Application No. PCT/EP2011/054511, filed Mar. 24, 2011, which claims the benefit of U.S. Provisional Patent Application No. 61/317,024, filed Mar. 24, 2010, the disclosures of which are hereby incorporated by reference in their entireties, including all figures, tables and amino acid or nucleic acid sequences.

FIELD OF THE INVENTION

The present invention relates to reverse micelle system based on sterols, acylglycerols, phospholipids or sphingolipids and metal ions. Reverse micelle system of the invention is able to cross mucosa and cellular membranes. It thus allows vectorization of metal ions to target sites. It is advantageously useful in the pharmaceutical and dietetic fields.

BACKGROUND OF THE INVENTION

Over the last years, various approaches have been proposed to improve the delivery of drugs at the target site. First, the drug must be administered by a suitable and easy route, such as orally or rectally, and second the active ingredient must be delivered at the target cells under an active form. There is no device currently available allowing such a vectorized transport of active molecules.

Many publications and patents describe methods for encapsulating active ingredients into nano or micro-particles, but the issue, to date unsolved, is to provide both an easy route of administration different from the injectable route, such as oral and buccal routes, and an efficient delivery of the active product at the target sites.

The inventors have previously uncovered that stirring two types of lipids with some metallic salts allowed to increase salt bioavailability and consequently to obtain same therapeutic activity with 1000 to 5000 times lower doses; the potential toxicity of said salts could then be reduced [see U.S. Pat. No. 6,129,924, WO 02/36134 and WO 2004/075990, for instance].

The inventors in particular identified novel products indicated under the term "organometallic complexes", and obtained by reaction between a derivative of vanadium in oxidation state 4 or 5 and two organic compounds isolated from plant extracts and respectively constituted of sitosterol and acylglycerols.

The inventors also discovered that similar complexes could be prepared from other derivatives of metals wherein the metal is for instance known for its antidiabetic activity.

They also discovered that similar complexes could be obtained from the organic derivatives mentioned previously and various cations of metals useful as biocatalysts in living metabolism, these complexes being particularly effective agents as vectors of said cations. Such vectorization of metallic cations affords an important decrease of the toxicity of administered cations compared to their administration in the absence of micelles as previously described. Actually, the use of such complexes, as described in WO2006/048773, allows efficient vectorization of the cations to target sites and thus allows administration of far lower amounts of metal. For instance, the use of these complexes affords obtaining the same therapeutic activity with 1000 to 10000 times lower doses.

Such complexes have been shown effective to vectorize metallic cations in small quantities, for instance lower than 80 µg of lithium, per ml of formulation. If such amounts are sufficient to compare the therapeutic activity of cations in animals, transposition to the human scale requires higher amounts of cations to be administered. The stability of microemulsions containing higher quantities of metal is not always satisfactory to allow their development as delivery systems for drugs and/or dietetic compounds for example.

Incorporation of a phospholipid or a sphingolipid, in particular in specific amounts, in the formulation of microemulsions comprising higher doses of metal ions surprisingly triggered an important increase in their stability.

The present invention describes new microemulsions formulations able to vectorize high quantities of metal ions, process of preparation and use thereof as delivery systems for drugs and/or dietetic compounds. "High" amounts refer here to amounts sufficient to obtain a therapeutic activity at the human scale, but that remain far lower than the amounts of cations delivered in absence of complexes. The reverse micelle system of the present invention may for instance allow vectorization of up to 1500 µg of metal per ml of formulation.

This formulation advantageously renders possible the control and optimisation of the composition comprising micelles for their uses in the pharmaceutical and dietetic fields.

SUMMARY OF THE INVENTION

The present invention relates to a mucosally applied delivery system for the release of metal ions as well as the compositions and methods for preparing the delivery system. Herein described are reverse micelle systems designed to reach this goal in a safe and controlled manner. The reverse micelle systems are able to be absorbed through mucosa and to vectorize metallic cations under a protected form to any tissue of the organism.

The reverse micelles of the invention comprise more specifically at least one metal ion, a sterol, an acylglycerol, a phospholipid or a sphingolipid, an alcohol, and water.

The reverse micelles can be prepared according to a method described below using at least a sterol, an acylglycerol, a phospholipid or a sphingolipid, an alcohol and water.

Said micelles are more particularly obtainable by the following method:
  (a) Contacting (i) sterol, preferably sitosterol or cholesterol, (ii) acylglycerol, preferably diacylglycerol, (iii) phospholipid, preferably phosphatidylcholine, or sphingolipid, (iv) alcohol, (v) water, preferably purified water, and (vi) at least one metal ion,
  (b) Stirring mixture obtained in step (a), at 40° C. or less, and for a time sufficient to obtain formation of reverse micelles.

The parameters of stirring, for instance duration and speed of mechanical stirring, can be readily determined by any one skilled in the art and depend on experimental conditions. In practice, these parameters are such that a microemulsion is obtained; the speed is determined so as to enable formation of a visually limpid formulation, and duration of the stirring is such that the stirring may be stopped a few minutes after obtaining the visually limpid formulation.

The present invention further relates to a composition comprising reverse micelles of the invention and a pharmaceutically acceptable carrier, excipient or support.

DETAILED DESCRIPTION OF THE INVENTION

The following description is of preferred embodiments by way of examples only and without limitation to the combination of features necessary for implementing the invention.

Reverse Micelles

The reverse micelle system according to the invention is characterized as a microemulsion comprising a dispersion of water-nanodroplets in oil. The dispersion is stabilised by two surfactants (acylglycerol, more preferably a diacylglycerol and a phospholipid, more preferably phosphatidylcholine, or a sphingolipid) and a co-surfactant (alcohol) that are most likely at the water/oil interface. The reverse micelle phase can be defined as a system wherein water forms the internal phase and the hydrophobic tails of the lipids form the continuous phase. Reverse micelles containing oil(s), surfactant(s), co-surfactant(s), and an aqueous phase are also characterized as water-in-oil microemulsions. These microemulsions are thermodynamically stable and visually limpid.

Generally, the size of micelles according to the invention is very small, more particularly, it is less than 10 nm; more specifically it is less than 8 nm and more preferably less than 6 nm. The size may vary with the quantity of added water and phospholipid or sphingolipid. The present invention relates more particularly to reverse micelles with an aqueous core of around 4 nm, preferably 3 to 5 nm, more preferably from 3.5 to 5 nm, in particular from 3.7 to 4.5 nm.

The reverse micelles and the size of their aqueous core can be characterized by various methods, including:

Small Angle X-Ray Scattering (SAXS)
Neutrons Scattering
Transmission Electron Microscopy (TEM)
Dynamic Light Scattering (DLS)

The ratios of the lipidic constituents (including sterol, acylglycerol and phospholipid or sphingolipid) in the reverse micelle system according to the invention can vary. For instance, the weight ratio sterol/acylglycerol can range from 0.015 to 0.05, more particularly from 0.03 to 0.04. The weight ratio phospholipid or sphingolipid/acylglycerol can range from 0.05 to 0.40, in particular from 0.06 to 0.25. The weight of phospholipid or sphingolipids respectively corresponds to the total weight of the mixture of phospholipids or sphingolipids, for instance the weight of lecithin, used in the formulation. Similarly, the weight of acylgylycerol corresponds to the total weight of the mixture usually containing an acylglycerol, or a mixture of acylglycerols, with glycerol and fatty acids derived from said acylglycerol(s).

The compounds of the reverse micelle system can be analyzed by appropriate means. More specifically, sterols can be identified by gas chromatographic analysis and acylglycerol by high-performance liquid chromatography (HPLC), in particular with a light scattering detector, on a silica column, in the presence of an eluent, e.g. isocratic acetonitrile. Gas chromatography can also be used to analyze diacylglycerols. Phospholipids and sphingolipids can be analyzed by high-performance liquid chromatography (HPLC), with a diol column with a light scattering detector.

Reverse micelles are dynamic systems. Brownian motion causes perpetual collisions of micelles, which lead to coalescence of micelles and exchange of the aqueous cores. Separation and regeneration of micelles occur and allow chemical reactions between different solutions. The exchange rate between micelles increases in particular with temperature, the length of hydrocarbon chains of the surfactant, and the ratio water/surfactant. Within the context of the invention, aqueous cores of micelles must have a specific size allowing metal ions to be stabilised in the prepared micelles. As mentioned above, the size of the aqueous core is preferably around 4 nm, more preferably from 3 to 5 nm, more specifically from 3.5 to 5 nm, in particular from 3.7 to 4.5 nm.

Reverse micelles may exist in the system of the invention as different structural organizations, such as spheres, cylinders or branched cylinders for instance.

Without being bound to any theory, it seems that inclusion of a phospholipid or a sphingolipid, in particular in specific amounts, in the reverse micelle system allows formation of micelles with greater diameter and volume, thus allowing vectorization of greater amounts of metal ions. This increase in vectorized cations amounts affords vectorization of sufficient amounts to obtain a therapeutic activity in human.

The reverse micelle system of the invention ensures absorption of the compounds to be delivered across mucosa, preferably across mouth, nasal and/or rectal mucosa, more preferably across mouth mucosa. Also, reverse micelles of the present invention provide an important bioavailability with low variability of absorption.

Method for Preparing Reverse Micelles

In a particular embodiment, the invention relates to a method for preparing reverse micelles presenting an aqueous core of around 4 nm, preferably from 3 to 5 nm, more preferably from 3.5 to 5 nm, in particular from 3.7 to 4.5 nm and involving at least one metal ion, a sterol, an acylglycerol, a phospholipid or a sphingolipid, an alcohol, and water, wherein said method comprises the following steps:

(a) Contacting (i) sterol, (ii) acylglycerol, preferably diacylglycerol, (iii) phospholipid, preferably phosphatidylcholine, or sphingolipid, (iv) alcohol, (v) water, preferably purified water, and (vi) at least one metal ion, (b) Stirring mixture obtained in step (a), at 40° C. or less, and for a time sufficient to obtain formation of reverse micelles.

The obtained and recovered reverse micelles are then particularly useful as a delivery system for metal ions. Step (b) of the process is of particular importance since it allows reverse micelles to be obtained, said reverse micelles being then useful as a transport system for delivering metal ions at target sites. Target sites may for instance be cells of a specific tissue.

In a particular embodiment, the metal ion is first solubilised in water (preferably purified water) to form an aqueous mixture. Said aqueous mixture is then introduced into the oily mixture (step (a)). Said oily mixture preferably comprises at least a sterol, an acylglycerol, a phospholipid or a sphingolipid and an alcohol.

The compounds involved in step (a) will be described in more details below.

Stirring of the mixture obtained by step (a) is carried out at a temperature less than or equal to 40° C., specifically ranging from 15° C. to 40° C., or from 25° C. to 40° C., or more specifically from 30° C. to 37° C. The time sufficient can vary in particular upon the used stirring technique. The time of stirring is anyhow the time needed to convert the initial mixture into a visually limpid reverse micelle solution.

One skilled in the art knows how to select excipients or components that may be used along with the composition according to the present invention in order to keep their beneficial properties. In particular, the presence of glycerol can, when introduced in large amount, prevent the formation of reverse micelles or break the reverse micelle system. More specifically, no more than 2.5% (percent expressed by weight of glycerol/weight of acylglycerol) is used for the preparation of the reverse micelles of the present invention.

Other compounds can be introduced in step (a). One can cite for instance colouring agents and/or flavouring substances.

In an advantageous manner, the compounds cited above or the commercially available mixtures containing them are the only ingredients introduced to prepare the micelle system and consequently the only ones present in the micelle system of the invention.

Stirring of step (b) may for instance be performed by mechanical stirring.

The common materials may be propellers whose fast movements generate turbulences and swirls allowing interpenetration of particles and formation of reverse micelles within the mixture.

Mechanical stirring speed is preferably ranging from 100 to 2 000 r/minute, more preferably from 300 to 700 r/minute. The implemented volumes, device, and stirring speed depend on and should be adapted with the reactants and amounts thereof.

As described above, temperature of the mixture should not exceed 40° C. as to avoid degradation of the reactants. Temperature is more specifically ranging from 15° C. to 40° C., or from 25° C. to 40° C., or even more specifically from 30° C. to 37° C.

Reverse Micelles Compounds
Acylglycerol

Acylglycerols useful for the preparation of the reverse micelle system according to the invention can be isolated from the majority of animals and more preferably plants.

Acylglycerols include mono- di and triacylglycerols. In a particular embodiment, acylglycerols preferentially used in the present invention present the following formula (I):

in which:
$R_1$ is an acyl residue of a linear or branched, saturated or unsaturated fatty acid having between 14 and 24 carbon atoms, a hydrogen atom, or a mono-, di- or tri-galactose or glucose;
$R_2$ is an acyl residue of a linear or branched, saturated or unsaturated fatty acid having between 2 and 18 carbon atoms;
$R_3$ is an acyl residue of a linear or branched, saturated or unsaturated fatty acid having between 14 and 24 carbon atoms, or a hydrogen atom.

According to a particular embodiment, $R_1$ or $R_3$, preferably only one of $R_1$ and $R_3$, in particular only $R_1$, represents an acyl residue of oleic acid (C18: 1[cis]-9).

According to a particular aspect, $R_2$ has one unsaturated bond (e.g., ethylenic bond) and has advantageously 18 carbon atoms, preferably $R_2$ is an oleic acid residue (oleoyl group), one of its positional isomers with respect to the double bond (cis-6, 7, 9, 11 and 13) or one of its iso-branched isomers.

According to another particular aspect, $R_1$ represents an oleoyl group.

According to another particular aspect, $R_2$ represents an acetyl group.

According to another particular aspect, $R_3$ is a hydrogen atom.

As a general rule, oil containing a high concentration of oleic acid will be chosen as a useful source of acylglycerols according to the invention. Such oil usually contains a high proportion of acylglycerols useful according to the invention.

According to a particular aspect of the invention, the preferred diglycerols of fatty acids are selected in the group consisting of 1,2-dioleoylglycerol (or also named herein 1,2-diolein) and 1-oleoyl-2-acetyl glycerol.

A certain number of them, and more particularly those which are found to be the most active in the applications sought after, are also available commercially. This is the case particularly for 1-oleoyl-2-acetylglycerol and 1,2-dioleoylglycerol. Glycerol monooleate 40 contains about 33% of dioleoyl glycerol, and about 11% of 1,2-diolein and is pharmaceutically accepted (*European Pharmacopeia* (4$^{th}$ Edition), *USP* 25/NF20, and *Japanese Standard of food Additives*). Such product is for instance commercially available by Gattefossé Company under the name PECEOL®.

The acylglycerols are preferably incorporated or comprised in the composition or reverse micelle system in an amount by weight ranging from 50 g to 90 g with respect to 100 g of the total weight of the composition or reverse micelle system according to the invention. The amounts specified herein will be adapted with respect to the other compounds as to correspond more specifically to the weight ratios identified below.

Sterols

The sterols useful for the preparation of the reverse micelle system according to the invention are preferably natural sterols, such as cholesterol or phytosterols (vegetable sterols). Sitosterol and cholesterol are the preferred sterols useful for the reverse micelle system according to the invention.

Sitosterol and cholesterol are commercially available. More particularly, commercial sitosterol which is extracted from soya can be used. In such a product, the sitosterol generally represents from 50 to 80% by weight of the product and is generally found in a mixture with campesterol and sitostanol in respective proportions in the order of 15% each. Commercial sitosterol which is extracted from a variety of pine called tall oil can also be used. In general, it will be possible to use sitosterol in mixture with sitostanol. Preferably, said mixture comprises at least 50% sitosterol by weight of the mixture.

As mentioned above, the ratios of the lipidic constituents (sterols, acylglycerol and phospholipids or sphingolipids) in the reverse micelle system according to the invention can vary. Preferably, the weight ratio sterol/acylglycerol can range from 0.015 to 0.05, more particularly from 0.03 to 0.04. The weight of sterol corresponds in the present invention to the total weight of sterols used in the formulation, for instance the weight of phytosterol.

The sterols are preferably incorporated or comprised in the composition or reverse micelle system in an amount by weight ranging from 0.825 g to 4.5 g with respect to 100 g of the total weight of the composition or reverse micelle system according to the invention. The amounts specified herein will be adapted with respect to the other compounds as to correspond more specifically to the weight ratios identified above and/or below.

Phospholipids and Sphingolipids

Phospholipids are formed of a glycerol linked to 2 fatty acids and to a phosphate group. The variability of phospholipids relies on the fatty acids that are attached to the glycerol and on the chemical groups that are susceptible to link to the phosphate group. Phospholipids are, with sphingolipids, the major lipidic constituents of biological membranes.

Among phospholipids useful in the present invention may be cited phosphatidylethanolamine, phosphatidylserine, phosphatidylglycerol, diphosphatidylglycerol, phosphatidylinositol, and phosphatidylcholine.

In a particular embodiment, the phospholipid is phosphatidylcholine. Phosphatidylcholine is also known as 1,2-diacyl-glycero-3-phosphocholine or PtdCho.

Phosphatidylcholine is formed from a choline, a phosphate group, a glycerol and two fatty acids. It is actually a group of molecules, wherein the fatty acid compositions varies from one molecule to another. Phosphatidylcholine may be obtained from commercial lecithin that contains phosphatidylcholine in weight concentrations of 20 to 98%. The lecithin preferably used for the preparation of the reverse micelles according to the invention is Epikuron 200® and contains phosphatidylcholine at a concentration of more than 90%.

Sphingolipids are a class of lipids derived from the aliphatic amino alcohol sphingosine. Among sphingolipids that may be used in the present invention may be cited acylsphingosin, sphingomyelins, glycosphingolipids, and gangliosides.

The reverse micelles system of the invention may comprise phospholipids, sphingolipids, or a mixture of both types of compounds.

According to a specific embodiment, the reverse micelles system of the invention comprises phospholipids.

The weight ratio phospholipid and/or sphingolipid/acylglycerol in compositions or reverse micelle systems according to the invention is from 0.05 to 0.40, preferably from 0.06 to 0.25.

The phospholipids or sphingolipids are preferably incorporated or comprised in the composition or reverse micelle system in an amount by weight ranging from 1 g to 30 g, preferably from 5 to 20 g with respect to 100 g of the total weight of the composition or reverse micelle system according to the invention. The amounts specified herein will be adapted with respect to the other compounds as to correspond more specifically to the weight ratios identified above.

Alcohols

The alcohols useful for the preparation of the reverse-micelle system according to the invention are preferably linear or branched mono-alcohols from C2 to C6. Examples of alcohols are ethanol, 1-butanol, 2-butanol, 3-methyl-1-butanol, 2-methyl-1-propanol, 1-pentanol, 1-propanol, 2-propanol and any mixture thereof. In a particular embodiment of the invention, alcohol is ethanol.

The alcohol is preferably incorporated or comprised in the composition or reverse micelle systems in an amount by weight ranging from 5 g to 12 g with respect to 100 g of the total weight of the composition or reverse micelle system according to the invention.

Water

The water useful for the preparation of the reverse micelle system according to the invention is preferably purified water.

Water is preferably incorporated or comprised in the composition or reverse micelle systems in an amount by weight ranging from 1 g to 15 g, preferably from 5 g to 15 g, with respect to 100 ml of the total volume of the composition or reverse micelle system according to the invention.

One of ordinary skill in the art will adapt the amount of phospholipid or sphingolipid in the systems to the desired amount of water. For instance, increasing amount of water should imply increasing amount of phospholipid or sphingolipid in the systems.

Metal

Metal cations which may be used for preparing reverse micelle system according to the invention are any cation in an oxidation state of at least 1, and whose biocatalytic activity is known or remains to be discovered.

In the context of the present invention, the term "biocatalyst" will indicate these metals exert a catalytic activity on the biological systems.

Metal ions play an essential role in approximately a third of the enzymes (*Metal Ions in Biological Systems*, Jenny P. Glusker, Amy K. Katz and Charles W. Bock, *The Rigaku Journal, vol* 16, No. 2, 1999). They can have different types of actions:

modification of flows of electrons from the substrate or the enzyme, allowing the control of an enzymatic catalytic reaction, connection with the proteinic components of the enzyme to give it a space configuration allowing it to present its active sites, to allow an activity of oxidation-reduction when metal has several valences.

Metal will be selected according to the desired biological activity.

As examples, if a product is sought with hypolipidaemic activity, or hypoglycaemic and/or antidiabetic and/or insulinomimetic activity, a metallic derivative of vanadium, niobium, molybdenum, selenium, chromium, zinc or titanium may more particularly be chosen.

As examples, if a product is sought with neuroprotective activity, a metallic derivative of lithium may more particularly be chosen.

As examples, if a product is sought with an activity on oxidative stress, a metallic derivative of manganese may more particularly be chosen.

As examples, if a product is sought with an activity on osteoporosis, a metallic derivative of strontium may more particularly be chosen.

As examples, if a product is sought with an activity on cancers, in particular acute promyelocytic leukemia, a metallic derivative of arsenic may more particularly be chosen.

In these metal derivatives:

lithium is preferably in an oxidation state equal to 1, vanadium is advantageously in an oxidation state equal to 3, 4 or 5, preferably 4, manganese is in general in an oxidation state comprised between and 1 and 7, preferably 2, 3, 4, 6 or 7, selenium is advantageously in an oxidation state equal to 4 or 6, preferably 4, molybdenum is in general in an oxidation state comprised between 3 and 6, preferably 3, chromium is preferably in an oxidation state equal to 3, niobium is advantageously in an oxidation state equal to 4 or 5, preferably 5, arsenic is preferably in an oxidation state equal to 3, zinc is preferably in an oxidation state equal to 2, 3 or 4.

In a particular embodiment, the metal ion presents an oxidation state of at least 1.

Examples of metals adapted to other types of activity are indicated below:
- lithium in pathologies of the central nervous system, such as bipolar disorder, neurodegenerative diseases like Huntington's disease, Parkinson disease, Alzheimer disease, amyotrophic lateral sclerosis, multiple sclerosis, prevention of dementia, or disease due to a prion infection,
- antimony or tin, if the treatment of autoimmune diseases concerning, in particular, the nervous system, for example multiple sclerosis and cancerology, is desired,
- gold, in autoimmune diseases affecting the locomotor system, for example in rheumatoid arthritis,
- vanadium in diabetes type 2, insulin resistance and metabolic syndrome,
- ruthenium or palladium in respiratory tumors or neoplasias,
- tin, in acquired immunodeficiency syndrome,
- selenium in cancerology,
- strontium in osteoporosis,
- arsenic in cancers, in particular acute promyelocytic leukemia,
- manganese in disease linked to oxidative stress.

In a particular embodiment, the metal cation is selected in the group consisting of lithium, zinc, niobium, vanadium, selenium, molybdenum, chromium, antimony, tin, gold, ruthenium, palladium, platinum, strontium, arsenic, and manganese.

Metal ions may be introduced in the reverse micelles of the invention as metal salts.

By way of examples, particularly useful metal derivatives according to the invention are selected from sulphates, hydrates, halides, in particular chlorides, citrates, carbonates and any other water-soluble salt.

It will be possible in some cases to use ammonium salts, methoxides of alkali metals or alkaline earth metals which can be dissolved in water or sometimes in alcohols. However water-soluble salts will be preferred.

Any metal having a water-soluble salt can be introduced into the reverse micelles according to the invention. The choice of metal will vary upon the desired therapeutic activity.

Anyone skilled in the art is aware of the inherent difficulties of the therapeutic use of metal cations due to the toxicity of said metal cations in an effective active amount: well-known examples are the lithium salts used in psychiatric or neurologic disorder or the platinum, ruthenium or palladium salts used in cancerology. Inclusion of such cations in reverse micelle systems of the invention allows using the cations in low amounts.

As indicated above, a preferred metal is a metal exhibiting a biocatalytic activity.

Since metal ions according to the invention can be delivered efficiently to the target site(s), the therapeutic activity is obtained with amounts of metal divided by 100 to 1 000 compared to the activity obtained with a salt or an organic derivative of the same metal when not included in the reverse micelle system of the invention.

The weight concentration of the cations in the microemulsion is more specifically calculated with a density of $0.94\pm0.03$ for the microemulsion.

The density is generally measured at room temperature and atmospheric pressure.

Reverse Micelle System and use Thereof

The reverse micelles of the invention allow the metal ions included therein to be administered and transported to target sites, in particular cells.

It is known today that a reverse micelle system can be used for the preparation of nanomaterials, which act as micro reactors. The activity and stability of bio molecules can be controlled, mainly by the concentration of water in the reverse micelle system.

An object of the invention concerns a pharmaceutical composition comprising reverse micelles as defined above and at least a pharmaceutically acceptable carrier, excipient or support.

According to a specific embodiment, the pharmaceutical composition according to the invention comprises from 5 to 20 g of phospholipid or sphingolipid with respect to 100 g of composition, and from 5 to 15 g of water with respect to 100 ml of composition.

In a specific embodiment, the pharmaceutical composition of the invention is used for the delivery, more specifically the mucosal delivery, of metal ions.

According to particular embodiments, the pharmaceutical composition is in the form of a capsule, a caplet, an aerosol, a spray, a solution or a soft elastic gelatin capsule. A further object of the invention concerns the use of reverse micelles as defined above for preparing a pharmaceutical composition intended for the delivery, more specifically the mucosal delivery, of metal ions.

Another object of the invention concerns a method for the delivery of at least one metal ion to a mammal (in particular human), said method comprising administering the reverse micelle composition as defined above to the mammal. In a specific embodiment, the present invention provides a method for the mucosal delivery of at least one metal ion, said method comprising mucosally administering to said mammal (in particular human) a reverse micelle composition as defined above.

The present invention provides a method for the prevention, treatment, or improvement of chronic diseases. In a specific embodiment, the present invention provides a method for the prevention, treatment or improvement of one or more symptoms associated with a disease or disorder in relation with the catalytic activity of the used metal ion, said method comprising mucosally administering to a subject in need thereof an effective amount of a reverse micelle composition as defined above and comprising at least one metal ion useful in the prevention, treatment or improvement of one or more symptoms associated with said disease or disorder.

As pharmaceutically acceptable excipient, vehicle or carrier, any excipient, vehicle or carrier well-known to the person skilled in the art may be used. Other additives well-known to the person skilled in the art such as stabilisers, drying agents, binders or pH buffers may also be used. Preferred excipients in accordance with the invention promote adherence of the finished product to the mucosa.

The present invention further concerns the use of a pharmaceutical composition as described above for the delivery of at least one metal ion to a mammal, said delivery comprising mucosa administration of the pharmaceutical composition.

The compositions of the invention can be administered in different ways, in particular via mucosal tissue absorption, with a buccal, nasal, vaginal or digestive absorption.

Pharmaceutical compositions as described above may be used in particular for the prevention, treatment or improvement of the symptoms of a disease or disorder selected among pathologies of the central nervous system (CNS), neurodegenerative diseases, autoimmune diseases, type 2 diabetes, insulin resistance, metabolic syndrome, cancers, such as respiratory tumors or acute promyelocytic leukemia, acquired immunodeficiency syndromes, cancerology, osteoporosis, diseases linked to oxidative stress, bipolar disorders, depression, and inflammatory disorders.

Metal ions in reverse micelle system formulated according to the invention are preferably able to cross the blood brain barrier. Consequently, they can be useful in the treatment of central nervous system (CNS) disorders, in particular genetic, tumoral, viral and/or degenerative diseases in the CNS.

A particular embodiment concerns a pharmaceutical composition as described above, wherein the metal ion is lithium, and that is used for the prevention, treatment or improvement of the symptoms of a disease or disorder selected among pathologies of the CNS and neurodegenerative diseases.

A further particular embodiment concerns a pharmaceutical composition as described above, wherein the metal ion is vanadium, and that is used for the prevention, treatment or improvement of the symptoms of a disease or disorder selected among type 2 diabetes, insulin resistance and metabolic syndrome.

A further particular embodiment concerns a pharmaceutical composition as described above, wherein the metal ion is manganese, and that is used for the prevention, treatment or improvement of the symptoms of a disease or disorder selected among disorders linked to oxidative stress.

A further particular embodiment concerns a pharmaceutical composition as described above, wherein the metal ion is arsenic, and that is used for the prevention, treatment or improvement of the symptoms of cancers, such as acute promyelocytic leukaemia.

A further particular embodiment concerns a pharmaceutical composition as described above, wherein the metal ion is strontium, and that is used for the prevention, treatment or improvement of the symptoms of osteoporosis.

"Subject" refers to an organism to which the metal ions of the invention can be administered. The subject may be a non-human animal, preferably a mammal. The preferred subject is a human subject.

As used herein, the terms "mucosa" and "mucosal" refer to a mucous tissue such as of the respiratory, digestive, or genital tissue. "Mucosal delivery", "mucosal administration" and analogous terms as used herein refer to the administration of a composition through a mucosal tissue. "Mucosal delivery", "mucosal administration" and analogous terms include, but are not limited to, the delivery of a composition through bronchi, gingival, lingual, nasal, oral, vaginal, rectal, and gastro-intestinal mucosal tissue.

In a preferred embodiment of the invention, the reverse micelle composition of the invention is mucosally administered as a capsule, a caplet, an aerosol, a spray, a solution or a soft elastic gelatin capsule. The compositions of the invention can for instance be introduced in liquid form into capsules which release their contents in the mouth or on any mucous tissue. Preferably, the reverse micelle compositions of the invention are administered to a mammal, more preferably a human, to treat a disease or disorder.

The following examples are intended to exemplify the operation of the present invention but not to limit its scope.

EXAMPLES

Example 1

Evaluation of Water Incorporation Impact on Formation and Size of Reverse Micelles in Absence of Lecithin The aim of this study was to evaluate by X ray diffraction method and visual determination the impact of water content on the formation of thermodynamically stable microemulsions and the size of reverse micelles dispersed therein.

10 formulations of reverse micelles with different percentages of water were prepared according to the procedure below.

0.7 g of phytosterol were dissolved in 1.4 g of absolute ethanol by magnetic stirring at 300 r/min for 15 minutes at 37° C. Glycerol monooleate was added thereto and magnetic stirring was carried out at 500 r/min for 45 minutes at 37° C. Purified water was added to this oil mixture and stirred between at 700 rpm for 30 minutes at 37° C. to form "empty" reverse micelles.

The different formulations are summarized in the table below.

| Sample | Water content (%) | Glycerol monooleate | Water |
|---|---|---|---|
| 1 | 1 | 25.8 g | 0.3 g |
| 2 | 2 | 25.5 g | 0.6 g |
| 3 | 3 | 25.2 g | 0.9 g |
| 4 | 4 | 24.9 g | 1.2 g |
| 5 | 5 | 24.6 g | 1.5 g |
| 6 | 6 | 24.3 g | 1.8 g |
| 7 | 7 | 24.0 g | 2.1 g |
| 8 | 8 | 23.7 g | 2.4 g |
| 9 | 9 | 23.4 g | 2.7 g |
| 10 | 10 | 23.1 g | 3.0 g |

"Empty" reverse micelles were prepared by increasing quantity of water from 1% to 10% with increment of 1% (the percentage of water is expressed by weight of water/total volume of the composition, density of 0.94). The percentage of absolute ethanol (5%) and phytosterol (2.5%) (weight/total weight of the composition) were unchanged for all these products.

The formation of thermodynamically stable microemulsions was evaluated by the visual determination of their limpidity.

Lattice parameters are obtained by X-ray diffraction and they are assumed to correspond to the size of reverse micelles of the invention. Samples were introduced in 1.5 mm diameter glass capillaries and a transmission configuration was used. A cupper rotating anode X-Ray source (functioning at 4 kW) with a multilayer focusing "Osmic" monochromator giving high flux ($10^8$ photons/sec) and punctual collimation were employed. An "Image plate" 2D detector was used. Diffraction curves were obtained giving diffracted intensity as a function of the wave vector q. Diffracted intensity was corrected by exposition time, transmission and intensity background coming from diffusion by an empty capillary. Reverse micelle sizes were calculated with the formula: $d=2\pi/q_{max}$ (q max is the wave vector corresponding to the maximal diffracted intensity).

Figure 1A:
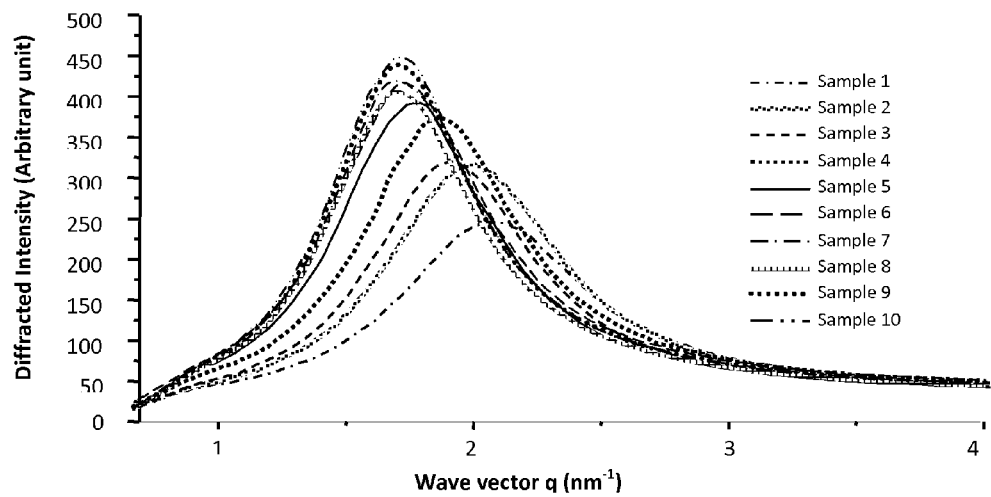
FIG. 1: Evaluation of the impact of the rate of incorporated water in absence of lecithin on diffraction curves (FIG. 1a) and size (FIG. 1b) of reverse micelles.
Figure 1B:
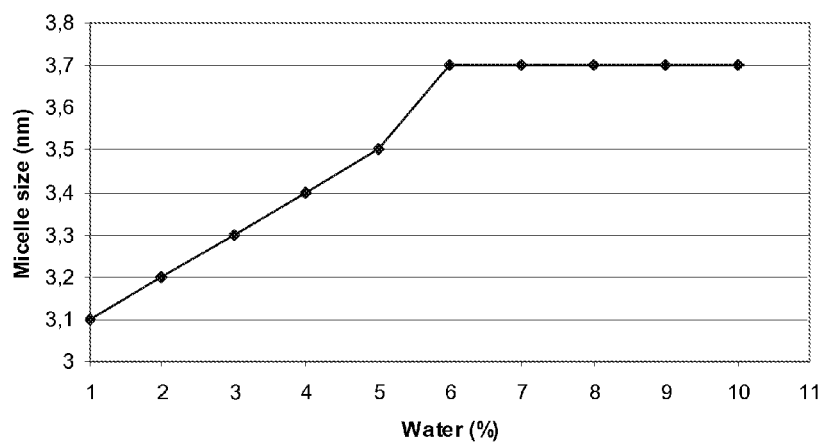

Diffraction curve of 10 samples prepared according to above procedure are shown in FIG. 1a, which clearly demonstrates that between 1% and 6% of incorporated water, the qmax value decreases when the percentage of water increases. FIG. 1b shows that between 1% and 6% of incorporated water, the size of reverse micelles increases from 3.1 to 3.7 nm when the percentage of water increases. In contrast, from 7% of incorporated water, the size of reverse micelles stops increasing.

Furthermore, the visual analysis shows that from 1 to 5% of incorporated water, the products are limpid. From 6% of water, the products become more and more turbid.

These results clearly show that formulations formed in absence of lecithin are unstable over a certain amount of water (6%). They additionally show that the micelles formulated without lecithin cannot exceed a given size even when increasing the amount of water in the formulation.

Example 2

Evaluation of Water Incorporation Impact on Formation and Size of Reverse Micelles in Presence of Lecithin The aim of this study was to evaluate by X ray diffraction method and visual determination the impact of water content on the formation of thermodynamically stable microemulsions and the size of reverse micelles dispersed therein in presence of increasing rate of lecithin.

3 formulations of reverse micelles with different percentages of water and lecithin were prepared according to the procedure below.

Commercially available lecithin was dissolved in 8.5 g absolute ethanol by magnetic stirring at 300 r/min for 10 minutes at room temperature. 2.3 g of phytosterol were added to the mixture and stirred in the same conditions. Glycerol monooleate was added thereto and magnetic stirring was carried out at 500 r/min for 45 minutes at 37° C. to form an oil mixture. Purified water was added to the oil mixture and stirred at room temperature by magnetic stirring at 700 r/min for 30 minutes to form "empty" reverse micelles.

The different formulations are summarized in the table below.

| Sample | Lecithin | Glycerol monooleate | Water | Oil mixture |
| --- | --- | --- | --- | --- |
| 11 | 0 g (0%) | 79.3 g | 20.4 mg (4%) | 453.9 mg |
| 12 | 9.4 g (10%) | 64.8 g | 45.0 mg (9%) | 433.8 mg |
| 13 | 14.1 g (15%) | 57.0 g | 60.0 mg (12%) | 423.3 mg |

"Empty" reverse micelles were prepared by varying quantity of water from 4% (sample 11) to 12% (sample 13) and lecithin from 0% (sample 11) to 15% (sample 13). Lecithin content is calculated from weight of lecithin/total weight of the composition and water content from weight of water/total volume of the composition (density of 0.94). The percentage of phytosterol was 2.5% (weight of phytosterol/total weight of the composition) and of absolute ethanol was 9% (weight of absolute ethanol/total weight of the composition) for all these samples.

The formation of thermodynamically stable microemulsions was evaluated by the visual determination of their limpidity.

The size of reverse micelles of these formulations was evaluated by X-ray diffraction experiments as described in example 1.

Figure 2A:
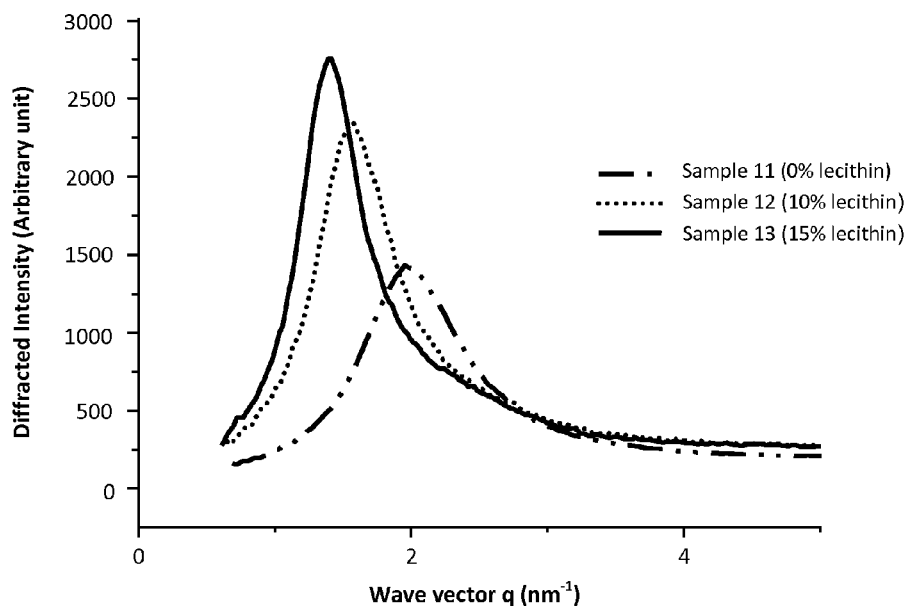
FIG. 2: Evaluation of the impact of the rate of incorporated water in presence of lecithin on diffraction curves (FIG. 2a) and size (FIG. 2b) of reverse micelles.
Figure 2B:
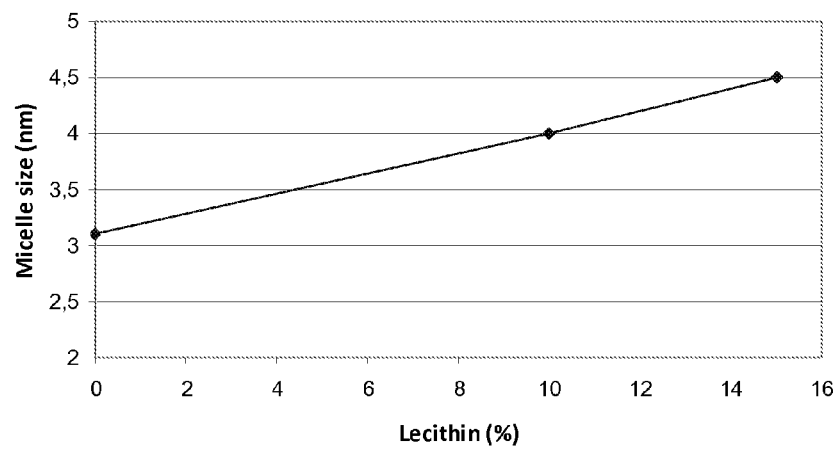

Diffraction curves of samples 11, 12, and 13 are shown in FIG. 2a which clearly demonstrates that the diffracted intensity increases and the qmax value decreases when the percentage of lecithin increases from 0 to 15%. FIG. 2b demonstrates that the size of reverse micelles increases from 3.1 to 4.5 nm when the percentage of lecithin increases from 0 to 15%. The visual analysis shows that these formulations are limpid.

Consequently, these experiments show that the addition of 15% of lecithin allows the formation of thermodynamically stable microemulsions with reverse micelle size of 4.5 nm and high percentages of water (12%). Addition of lecithin thus solves the drawbacks of reverse micelles formulated in absence of lecithin described in example 1.

Example 3

Reverse Micelles According to the Invention

The aim of this study was to evaluate by X ray diffraction method and visual determination the stability of a microemulsion according to the invention and the size of reverse micelles dispersed therein.

Sample A: 5.7 g of commercially available lecithin were dissolved in 8.5 g of absolute ethanol by magnetic stirring at 300 r/min for 10 minutes at room temperature. 2.4 g of phytosterol were added to the mixture and stirred in the same conditions. 68.6 g of glycerol monooleate were added thereto and magnetic stirring was carried out at 500 r/min for 1 hour at 37° C. 9.0 g of purified water containing 148.7 mg of vanadium sulfate (30.0 mg of metal vanadium) were added to this oil mixture and stirred at room temperature at 700 r/min for 15 minutes to form reverse micelles containing 300 µg metal vanadium/ml (density of 0.94). The formulation contains 6% of lecithin.

Lecithin content is calculated from weight of lecithin/total weight of the composition. The percentage of water was 9% (weight of water/total volume of the composition), of phytosterol was 2.5% (weight of phytosterol/total weight of the composition) and of absolute ethanol was 9% (weight of absolute ethanol/total weight of the composition).

Visual analysis showed that the microemulsion formulated with 6% of lecithin was limpid. The size of reverse micelles of this formulation was determined by X-ray diffraction experiments as described in example 1 to be 4 nm.

Example 4

Evaluation of the Impact of Sterol Origin on Formation and Size of Reverse Micelles The aim of this study was to evaluate by X ray diffraction method and visual determination the impact of the origin of the sterol (cholesterol or phytosterol) incorporated in the formulation on the formation of thermodynamically stable microemulsions and the size of reverse micelles dispersed therein.

4 formulations of reverse micelles containing vanadium or "empty" with phytosterol or cholesterol were prepared according to the procedures below:

Sample B: 84.5 g of lecithin were dissolved in 141.0 g of absolute ethanol by magnetic stirring at 150 r/min for 15 minutes at room temperature. 35.2 g of phytosterol were added to the mixture and stirred in the same conditions. 1074.3 g of glycerol monooleate were added thereto and magnetic stirring was carried out at 200 r/min for 1 h and 20 minutes at 37° C. 75.0 g of purified water containing 1.3 g of vanadium sulfate (0.27 g of metal vanadium) were added to this oil mixture and stirred at room temperature at 240 r/min for 15 minutes to form reverse micelles containing 180 µg metal vanadium/ml (density of 0.94).

Sample 14: 75.0 g of purified water were added to of the oil mixture prepared according to sample B and stirred at room temperature at 240 r/min for 15 minutes to form "empty" reverse micelles.

Sample C: 1.7 g of lecithin were dissolved in 2.8 g of absolute ethanol by magnetic stirring at 300 r/min for 10 minutes at room temperature. 0.7 g of cholesterol were added to the mixture and stirred in the same conditions. 21.5 g of glycerol monooleate were added thereto and magnetic stirring was carried out at 500 r/min for 45 minutes at 37° C. 0.5 g of purified water containing 8.5 mg of vanadium sulphate (1.8 mg of vanadium metal) were added to 8.9 g of this oil mixture and stirred at room temperature at 700 r/min for 15 minutes to form reverse micelles containing 180 µg metal vanadium/ml (density of 0.94).

Sample 15: 0.5 g of purified water were added to 8.9 g of the oil mixture prepared according to sample C and stirred at room temperature at 700 r/min for 15 minutes to form "empty" reverse micelles.

Reverse micelles containing 180 µg metal vanadium/ml (samples B and C) or without metal (samples 14 and 15) were formulated with phytosterol or cholesterol according to the above procedures. The percentage of water was 5% (weight of water/total volume of the composition), that of sterol was 2.5% (weight of sterol/total weight of the composition), that of lecithin was 6% (weight of lecithin/total weight of the composition) and that of absolute ethanol was 10% (weight of absolute ethanol/total weight of the composition) for all these samples.

The formation of thermodynamically stable microemulsions was evaluated by the visual determination of their limpidity.

The size of reverse micelles of these formulations was evaluated by X-ray diffraction experiments as described in example 1.

Figure 3:
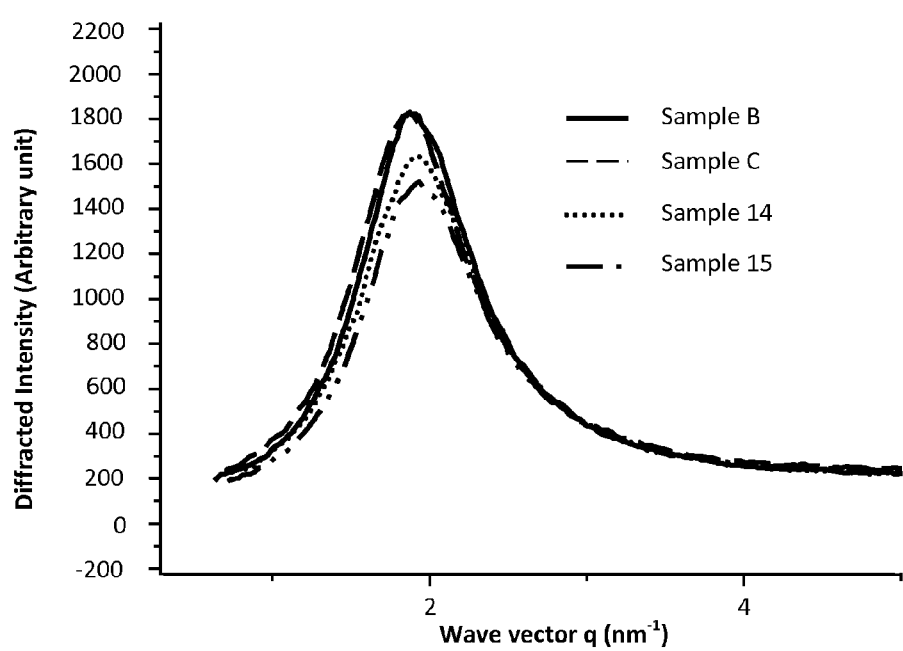
FIG. 3: Evaluation of the impact of the sterol origin on diffraction curves of reverse micelles.

Diffraction curve of samples B, C, 14 and 15 are shown in FIG. 3 which demonstrates that the $q_{max}$ values are the same for all the formulations. Then, the reverse micelle size is calculated at 3.3 nm. Furthermore, the visual observation of these products shows that all samples are limpid.

These experiments show that neither the sterol origin (phytosterol or cholesterol) nor the addition of vanadium at 180 µg/ml has an impact on the formation of thermodynamically stable microemulsions, nor on the size of reverse micelles dispersed therein.

Example 5

Evaluation of In Vivo Blood Repartition of Lithium Formulated in Reverse Micelles in Presence and Absence of Lecithin The aim of this study was to evaluate the repartition in blood components (plasma versus blood cells) of lithium formulated in 2 different reverse micelles formulations prepared according to procedures below (samples D and E) when delivered by rectal route.

Sample D: 1.4 g of phytosterol were dissolved in 4.0 g of absolute ethanol by magnetic stirring at 300 r/min for 10 minutes at room temperature. 48.9 g of glycerol monooleate were added thereto and magnetic stirring was carried out at 500 r/min for 45 minutes at 37° C. 2.4 g of purified water containing 25.7 mg of lithium carbonate (4.8 mg of metal lithium) were added to this oil mixture and stirred at room temperature at 700 r/min for 15 minutes to form reverse micelles containing 80 µg metal lithium/ml (density of 0.94).

Sample E: 3.4 g of lecithin were dissolved in 5.1 g of absolute ethanol by magnetic stirring at 300 r/min for 10 minutes at room temperature. 1.5 g of phytosterol were added to the mixture and stirred in the same conditions. 41.1 g of glycerol monooleate were added thereto and magnetic stirring was carried out at 500 r/min for 45 minutes at 37° C. 5.4 g of purified water containing 65.6 mg of lithium citrate (4.8 mg of metal lithium) were added to this oil mixture and stirred at room temperature at 700 r/min for 15 minutes to form reverse micelles containing 80 µg metal lithium/ml (density of 0.94).

Administered Products:

Sample D: reverse micelles prepared according to above procedure at 80 µg metal lithium/ml, delivered at 1 ml/kg by rectal route Sample E: reverse micelles prepared according to above procedure at 80 µg metal lithium/ml, delivered at 1 ml/kg by rectal route Spragues Dawley rats, 5 rats per group, were administered with 160 µg metal lithium/kg (80 µg/kg twice, 15 minutes interval) by rectal route with 2 formulations of lithium in reverse micelles (samples D and E). These products were administered slowly with a pipette into the lower rectum, immediately after the anal sphincter.

Animals were sacrificed 2 hours after the last treatment and blood samples were collected by intra-cardiac puncture. Centrifugation was performed at 4500 r/m for 5 minutes to separate plasma from blood cells.

Lithium concentration in plasma and blood cells was determined by Inductively Coupled Plasma Mass Spectrometry (ICPMS).

Figure 4:
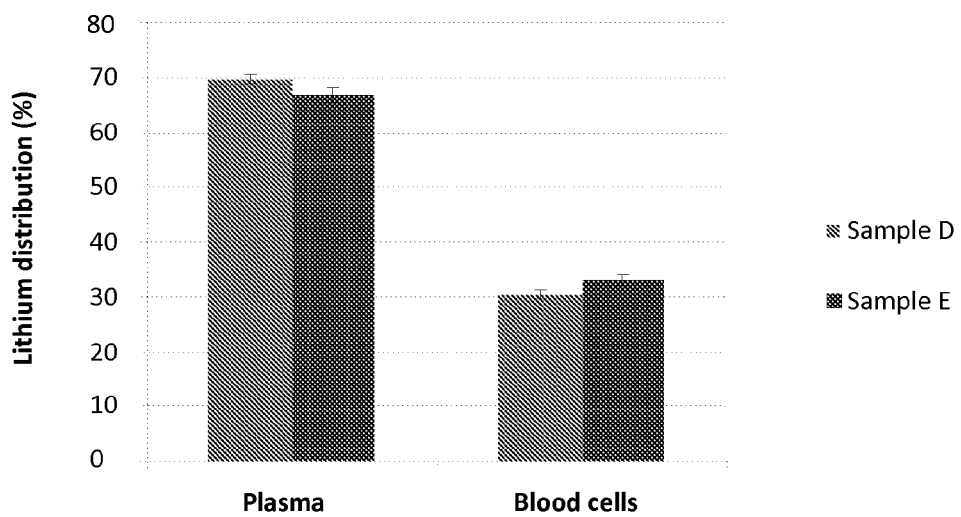
FIG. 4: In vivo evaluation of lithium distribution in blood components after administration of lithium in reverse micelles formulated with or without lecithin.

Results are shown in FIG. 4 which demonstrates that the addition of lecithin in reverse micelles of sample E did not decrease the delivery of lithium and did not change the repartition of lithium between plasma and blood cells. Reverse micelles according to the invention are thus as efficient as those not containing lecithin for delivery of low quantities of metal ions. They additionally allow delivery of greater amounts of metal ions than reverse micelles without lecithin.

Example 6

Evaluation of In Vivo Efficacy of Reverse Micelles Formulated with Lithium in EAE Mice Model of Multiple Sclerosis Multiple Sclerosis is the most common autoimmune inflammatory disease in the CNS. It is characterized by immune mediated demyelinisation and neurodegeneration of the CNS.

Experimental autoimmune encephalomyelitis (EAE) is a standard widely used experimental model of the clinical, immunological and neuropathological features of Multiple Sclerosis.

The aim of this study was to evaluate the efficacy of a pre-treatment with reverse micelles formulated with lithium according to procedures below (samples F and 16) in a chronic EAE model induced in mice.

Sample F: 3.4 g of lecithin were dissolved in 5.0 g absolute ethanol by magnetic stirring at 300 r/min for 10 minutes at room temperature. 1.4 g of phytosterol were added to the mixture and stirred in the same conditions. 41.2 g of glycerol monooleate were added thereto and magnetic stirring was carried out at 500 r/min for 45 minutes at 37° C. 5.4 g of water containing 32.7 mg of lithium citrate (2.4 mg of metal lithium) were added to this oil mixture and stirred at room temperature at 700 r/min for 15 minutes to form reverse micelles containing at 40 µg metal lithium/ml (density of 0.94).

Sample 16: 1.7 g of lecithin were dissolved in 2.5 g absolute ethanol by magnetic stirring at 300 r/min for 10 minutes at room temperature. 0.7 g of phytosterol were added to the mixture and stirred in the same conditions. 20.6 g of glycerol monooleate were added thereto and magnetic stirring was carried out at 500 r/min for 45 minutes at 37° C. 2.7 g of water were added to this oil mixture and stirred at room temperature at 700 r/min for 15 minutes to form "empty" reverse micelles.

Administered Products:
 Sample F: reverse micelles prepared according to above procedure at 40 µg metal lithium/ml, delivered at 1 ml/kg by rectal route from day 0 to day 50
 Sample 16: "empty" reverse micelles prepared according to above procedure, delivered at 1 ml/kg by rectal route from day 0 to day 50

To induce EAE, C57b1/6 were injected subcutaneously on days 0 and 7 with 150 µg of MOG peptide emulsified in complete Freund's adjuvant (Difco laboratories) supplemented with *Mycobacterium tuberculosis* H37 RA (Difco laboratories) at a final concentration of 5 mg/ml. In addition, on days 0 and 2 post-immunization (p.i.), mice were given 500 ng pertussis toxin (Sigma Aldrich Corporation) intraperitonally.

These mice (4 mice per group) were treated 5 days a week by rectal route with lithium formulated in reverse micelles (sample F) from day 0 to day 50 post immunization. Sample F at 40 µg metal lithium/kg was delivered slowly with a pipette into the lower rectum, immediately after the anal sphincter. Mice treated with "empty" reverse micelles (sample 16) in the same conditions (4 mice per group) were used as control.

Animals were weighed and scored for clinical signs of disease from day 10 post-immunization until day 50 (weekends excluded). Clinical assessment of EAE was performed daily according to the following criteria: 0=no disease signs, 1=tail weakness, 2=tail paralysis, 3=incomplete paralysis of one or two hind legs, 4=complete hind limb paralysis, 5=moribund, 6=death.

Animals were sacrificed on day 50 and spinal cords were harvested and frozen.

Quantification of axonal loss was performed on frozen spinal cord after neurofilament immunostaining. Cryostated sections of 14 µm were incubated firstly with an antibody directed against the 200 kDa neutrofilament protein (Serotec). They were incubated after with a secondary antibody labelled with biotin (Vector laboratories) and after with streptavidin-alexafluor (Molecular Probes). The axonal density was determined by visualisation of the neurofilament immunostaining using a fluorescent microscope (Zeiss Axioplan II).

Figure 5:
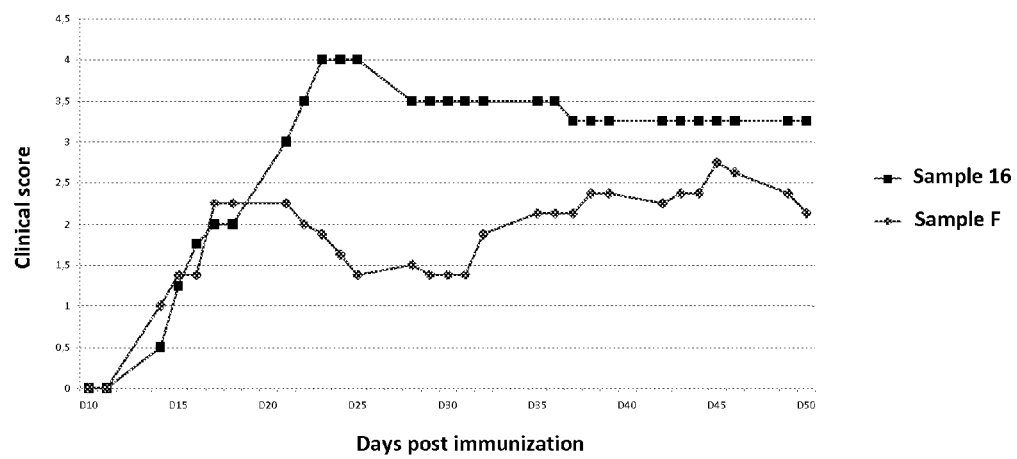
FIG. 5: In vivo evaluation of efficacy of lithium in reverse micelles on EAE clinical scores.

Results of clinical scores are shown in FIG. 5 which demonstrates that lithium in reverse micelles formulation containing lecithin (sample F) is effective at preventing the apparition of clinical signs during the acute phase of the disease and facilitates partial recovery during the chronic phase of the disease. In contrast "empty" reverse micelles are ineffective at decreasing clinical score (sample 16).

Figure 6:
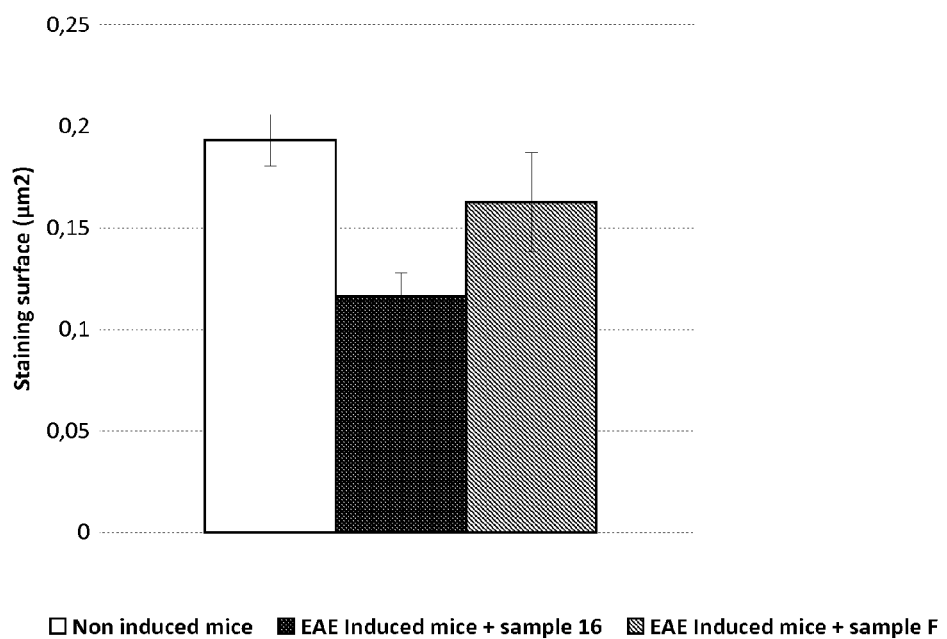
FIG. 6: In vivo evaluation of efficacy of lithium in reverse micelles on EAE axonal loss.

These results are confirmed by immunostaining assays presented in FIG. 6 which demonstrates that only the treatment with lithium in reverse micelles (sample F) prevents the axonal loss in spinal cord of EAE induced mice.

Example 7

Evaluation of In Vivo Efficacy of Reverse Micelles Formulated with Lithium in the R6/2 Mice Model of Huntington Disease Huntington disease (HD) is an inherited fatal neurologic disorder caused by an expansion of a CAG repeat in exon 1 of the huntingtin gene. The selective loss of a subset of brain cells (neurons) involves psychiatric, motor and cognitive disturbances.

R6/2 mice (Jackson Laboratory) are a transgenic model widely used as Huntington's disease model. They express human HD gene carrying approximately 120+/−5 (CAG) repeat expansions. Transgenic mice exhibit a progressive neurological phenotype that mimics many of the features of HD, including deficits of motor coordination, altered locomotor activity, impaired cognitive performance and seizures.

The aim of this study was to evaluate by a standardized battery of analysis the neuroprotective effect of lithium formulated in reverse micelles according to procedures below (samples G and H) in R6/2 mice compared to unformulated lithium administered by oral route. Motor coordination and balance were evaluated by rotarod test and swimming tank test. Cognitive performances were evaluated by swimming tank test.

Sample G: 1.0 g of phytosterol were dissolved in 3.0 g of absolute ethanol by magnetic stirring at 300 r/min for 10 minutes at room temperature. 36.5 g of glycerol monooleate were added thereto and magnetic stirring was carried out at 500 r/min for 45 minutes at 37° C. 1.8 g of purified water containing 9.7 mg of lithium carbonate (1.8 mg of metal lithium) were added to this oil mixture and stirred at room temperature at 700 r/min for 15 minutes to form reverse micelles containing 40 µg metal lithium/ml (density of 0.94).

Sample H: 9.4 g of lecithin were dissolved in 8.5 g of absolute ethanol by magnetic stirring at 300 r/min for 10 minutes at room temperature. 2.3 g of phytosterol were added to the mixture and stirred in the same conditions. 64.8 g of glycerol monooleate were added thereto and magnetic stirring was carried out at 500 r/min for 45 minutes at 37° C. 4.0 g of purified water containing 24.3 mg of lithium citrate (1.8 mg of metal lithium) were added to 38.2 g of this oil mixture and stirred at room temperature at 700 r/min for 15 minutes to form reverse micelles containing 40 µg metal lithium/ml (density of 0.94).

Sample 17: 4.0 g of purified water were added to 38.2 g of the oil mixture prepared according to sample H and stirred at room temperature at 700 r/min for 15 minutes to form "empty" reverse micelles.

Administered Products:
Sample G: reverse micelles prepared according to procedure above at 40 µg metal lithium/ml, delivered at 1 ml/kg/d by rectal route for at least 8 weeks
Sample H: reverse micelles prepared according to procedure above at 40 µg metal lithium/ml, delivered at 1 ml/kg/d by rectal route for at least 8 weeks
Sample 17: "empty" reverse micelles prepared according to procedure above, delivered at 1 ml/kg by rectal route for at least 8 weeks
Unformulated lithium: lithium in solution at 3.2 mg metal lithium/ml, delivered at 5 ml/kg/d by oral route (gavage) for at least 8 weeks As described below, R6/2 at 8-9 weeks old (apparition of the first clinical signs) were treated 5 days a week for at least 8 weeks with lithium in solution (group 4, 10 mice per group respectively) or formulated in reverse micelles (samples G and H). Lithium in solution was delivered by gavage at 16 mg metal lithium/kg using a plastic syringe fitted with a metal curved gavage tube. Samples G and H at 40 µg metal lithium/kg were delivered slowly with a pipette into the lower rectum, immediately after the anal sphincter (groups 1 and 2, 10 and 9 mice per group). R6/2 mice and wild type mice treated in the same conditions with "empty" reverse micelles (sample 17) (group 3 and 5, 8 and 6 mice per group) were used as control.

Rotarod tests were performed before and during the 4$^{th}$ and 6$^{th}$ week of treatment using a Rota Rod apparatus (UGO Basile 47600, rotating rod diameter 3 cm). After an acclimation test of 15 minutes, mice performed 2 trials at 5 rpm. The latency at which each mouse falls of the rod was recorded.

Swimming tests were performed using a tank filled to a depth of 20 cm with water and a visible escape platform located at the end of the tank side. During the 4$^{th}$ week of treatment, the latency to reach the platform and the swimming speed were recorded 5 times per day during 5 consecutive days.

Figure 7:
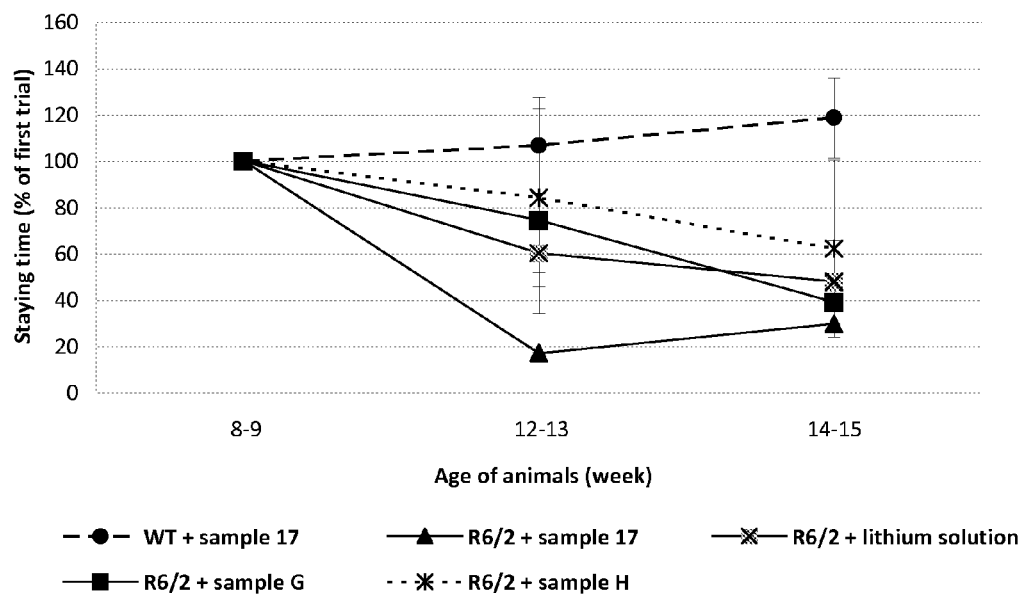
FIG. 7: In vivo evaluation of efficacy of lithium in reverse micelles on R6/2 motor coordination (rotarod test).

Results of rotarod test are shown in FIG. 7 which clearly demonstrates that both formulations of metal lithium in reverse micelles (samples G and H) maintain motor coordination of R6/2 mice. Furthermore, the effect of sample H formulated with lecithin administered at a dosage of 40 µg/kg was greater than those obtained with lithium by oral gavage at 16 mg/kg. In contrast, the treatment with reverse micelles containing no metal (sample 17) was ineffective at maintaining motor coordination of R6/2 mice.

Figure 8:
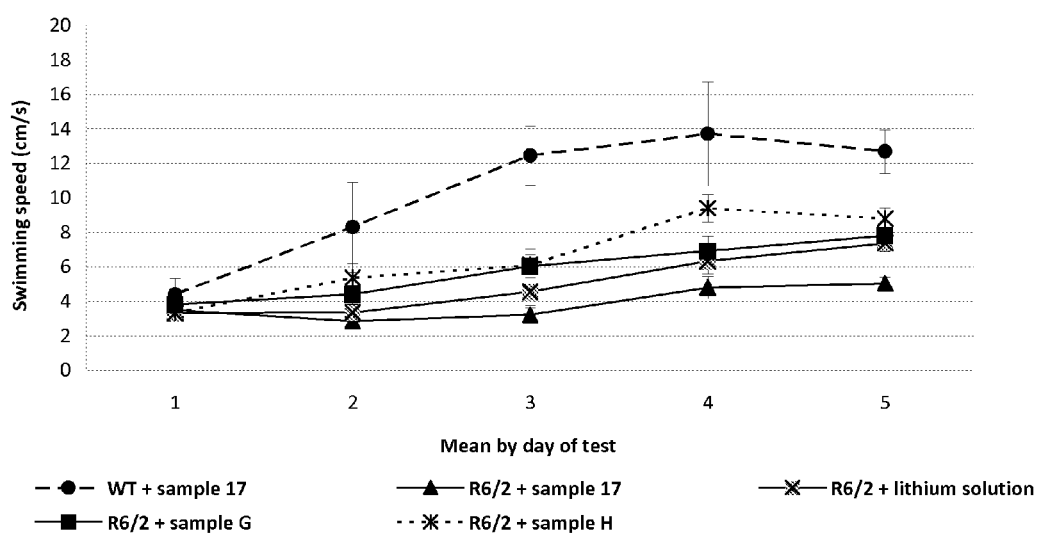
FIG. 8: In vivo evaluation of efficacy of lithium in reverse micelles on R6/2 motor performances (swimming tank test).

Results of swimming speed shown in FIG. 8 confirm that the R6/2 mice treated with lithium in both formulations of reverse micelles (samples G and H) have better motor performances than R6/2 mice treated with lithium by oral gavage at 16 mg/kg or with reverse micelles containing no metal (sample 17).

Figure 9:
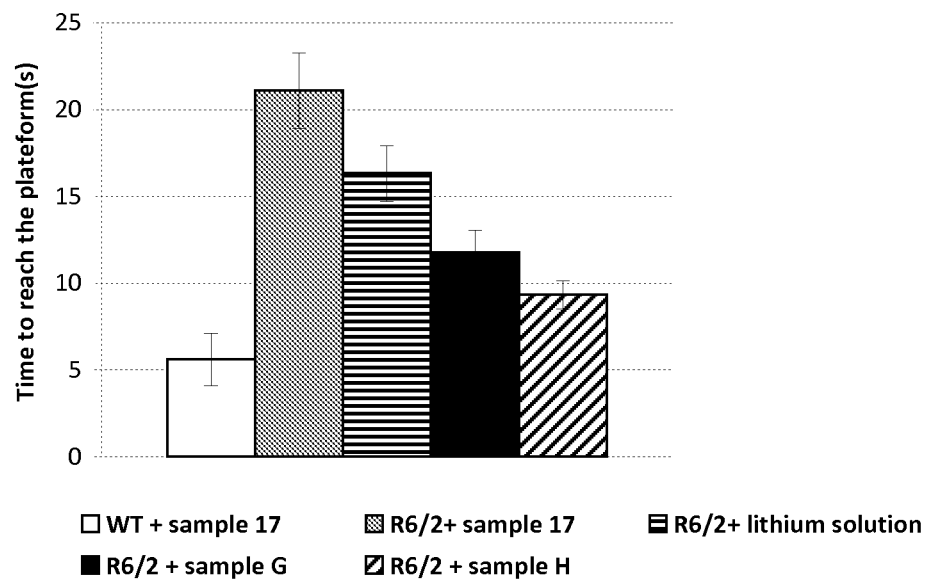
FIG. 9: In vivo evaluation of efficacy of lithium in reverse micelles on R6/2 cognitive performances (swimming tank test).

Results of cognitive performance are shown in FIG. 9 which clearly demonstrate that both formulations of metal lithium in reverse micelles (samples G and H) maintain the capacity of R6/2 to learn a simple task: choose the good direction to reach the platform. In contrast, reverse micelles containing no metal (sample 17) are ineffective at maintaining cognitive performances.

Reverse micelles according to the invention are thus as efficient as those not containing lecithin for delivery of low quantities of metal ions. They additionally allow delivery of greater amounts of metal ions than reverse micelles without lecithin.

| Mouse strain | Groups | Animal Number | Treatment | Delivered dose (µg/kg/d) | Delivered volume (ml/kg/d) |
| --- | --- | --- | --- | --- | --- |
| R6/2 | 1 | 10 | Sample G | 40 | 1 |
| | 2 | 9 | Sample H | 40 | 1 |
| | 3 | 8 | Sample 17 | 0 | 1 |
| | 4 | 10 | Lithium solution | 16000 | 5 |
| Wild type | 5 | 6 | Sample 17 | 0 | 1 |

Example 8

Formulation of Reverse Micelles with High Concentration of Lithium

The aim of this study was to formulate lithium in reverse micelles at 600 µg/ml according to the invention.

Sample I: 6.6 g of lecithin were dissolved in 5.9 g of absolute ethanol by magnetic stirring at 300 r/min for 10 minutes at room temperature. 1.6 g of phytosterol were added to the mixture and stirred in the same conditions. 45.3 g of glycerol monooleate were added thereto and magnetic stirring was carried out at 500 r/min for 45 minutes at 37° C. 6.3 g of purified water containing 567.7 mg of lithium citrate (41.9 mg of metal lithium) were added to this oil mixture and stirred at room temperature at 700 r/min for 15 minutes to form reverse micelles containing 600 µg metal lithium/ml (density of 0.94).

The formation of thermodynamically stable microemulsion according to the procedure above was evaluated by the visual determination of its limpidity after 3 months at 40° C.

This experiment shows that the addition of lecithin at 10% allows the formation of a limpid thermodynamically stable microemulsion with 600 µg/ml of metal lithium.

Example 9

Evaluation of In Vivo Efficacy of Reverse Micelles Formulated with Lithium in a Mice Model of Prion Disease Prion diseases or transmissible spongiform encephalopathies (TSEs) are a family of fatal and rare progressive neurodegenerative disorders caused by an infectious agent (Prion) composed of protein of misfolded form. This agent is able to induce abnormal folding of normal cellular prion proteins in the brain, leading to brain damage (neuronal loss, . . . ) and associated symptoms (dementia, . . . ).

C57bl/6J mice intracerebrally inoculated with brain homogenates infected with ME7 prion typically die between 165 and 175 days after inoculation. The disease is characterised by vacuolisation and neuronal loss, typically with a bilateral, symmetrical distribution as well as asctrocyte proliferation and prion protein accumulation.

The aim of this study was to evaluate the efficacy of treatment with reverse micelles formulated with lithium according to procedure below (sample J) on survival of mice infected with prion compared to unformulated lithium administered by oral route at higher dose.

Sample J: 23.5 g of lecithin were dissolved in 21.2 g of absolute ethanol by magnetic stirring at 300 r/min for 15 minutes at room temperature. 5.9 g of phytosterol were added to the mixture and stirred in the same conditions. 162.0 g of glycerol monooleate were added thereto and magnetic stirring was carried out at 500 r/min for 45 minutes at 37° C. 10.8 g of purified water containing 259.0 mg of lithium citrate (19.2 mg of metal lithium) were added to 102.0 g of this oil mixture and stirred at room temperature at 700 r/min for 30 minutes to form reverse micelles containing 160 μg metal lithium/ml (density of 0.94).

Sample 18: 10.8 g of purified water were added to 102.0 g of the oil mixture prepared according to sample J and stirred at room temperature at 700 r/min for 30 minutes to form "empty" reverse micelles.

Administered Products:
Sample J: reverse micelles prepared according to procedure above at 160 μg metal lithium/ml, delivered at 1 ml/kg/d by rectal route from 90 days after inoculation until death
Sample 18: "empty" reverse micelles prepared according to procedure above, delivered at 1 ml/kg by rectal route from 90 days after inoculation until death
Unformulated lithium: lithium in solution at 3.2 mg metal lithium/ml, delivered at 5 ml/kg/d by oral route (gavage) from 90 days after inoculation until death 20 μl of brain homogenates with 1% of ME7 prion were inoculated under general anaesthesia in brain of 5 weeks old C57bl/6 mice to induce disease. These mice were treated 5 days a week (week-ends excluded) with lithium in solution (14 mice per group) or formulated in reverse micelles (sample J) (14 mice per group) from 90 days after inoculation (at the post symptomatic phase) until death. Lithium in solution was delivered by gavage at 16 mg metal lithium/kg using a plastic syringe fitted with a metal curved gavage tube. Sample J at 160 μg metal lithium/kg was delivered slowly with a pipette into the lower rectum, immediately after the anal sphincter. Prion inoculated mice treated in the same conditions with "empty" reverse micelles (sample 18) (10 mice per group) were used as control.

Figure 10:
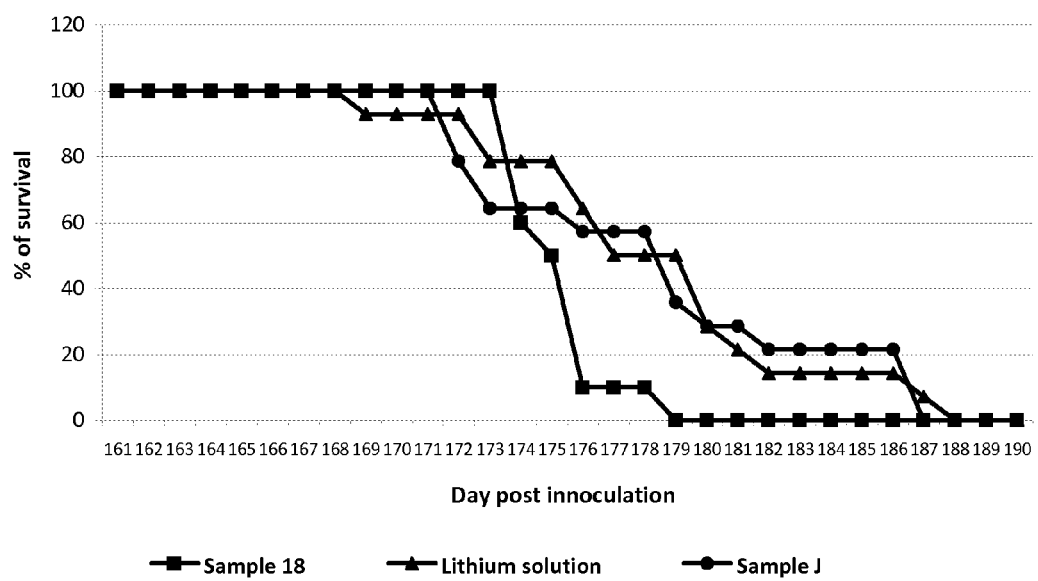
FIG. 10: In vivo evaluation of efficacy of lithium in reverse micelles on survival of mice inoculated with prion.

Results of survival are shown in FIG. 10 which clearly demonstrates that treatment with lithium in solution at 16 mg/kg or formulated in reverse micelles at 160 μg/kg (sample J) increase survival of prion infected mice compared to the treatment with reverse micelles containing no metal (sample 18).

This experiment shows that, with an equivalent efficacy, the formulation in reverse micelles according to the invention affords a lithium dose decrease by 100 times compared to the dose of lithium in solution.

Example 10

Evaluation of In Vivo Efficacy of Reverse Micelles Formulated with Lithium in a Behavioral Mice Model of Depression Bipolar disorder is a psychiatric disease describe as a mood disorder. It is defined by the alternation of mania and depression episodes. The treatment to stabilize mood is based on administration of high doses of lithium which has acute antimanic and antidepressant effects and long term prophylactic effects.

The aim of this study was to evaluate the efficacy of a pre-treatment with reverse micelles formulated with lithium according to procedure below (sample K) on a standard widely used behavioural mice model of depression (tail suspension test) compared to unformulated lithium administered by oral route at higher dose.

Sample K: 28.2 g of lecithin were dissolved in 24.5 g of absolute ethanol by magnetic stirring at 300 r/min for 10 minutes at room temperature. 7.0 g of phytosterol were added to the mixture and stirred in the same conditions. 194.4 g of glycerol monooleate were added thereto and magnetic stirring was carried out at 500 r/min for 45 minutes at 37° C. 7.2 g of purified water containing 161.6 mg of lithium citrate (12.0 mg of metal lithium) were added to 68.0 g of this oil mixture and stirred at room temperature at 700 r/min for 15 minutes to form reverse micelles containing 150 μg metal lithium/ml (density of 0.94).

Sample 19: 7.2 g of purified water were added to 68.0 g of the oil mixture prepared according to sample K and stirred at room temperature at 700 r/min for 15 minutes to form "empty" reverse micelles.

Administered Products:
Sample K: reverse micelles prepared according to procedure above at 150 μg metal lithium/ml, delivered at 1 ml/kg/d by rectal route during 4 weeks before the test
Sample 19: "empty" reverse micelles prepared according to procedure above, delivered at 1 ml/kg by rectal route during 4 weeks before the test
Unformulated lithium: lithium in solution at 3.2 mg metal lithium/ml, delivered at 5 ml/kg/d by oral route (gavage) during 4 weeks before the test C57bl/6 mice were treated 5 days a week (week-ends excluded) during 4 weeks with lithium in solution (12 mice per group) or formulated in reverse micelles (sample K) (12 mice per group). Lithium in solution was delivered by gavage at 16 mg metal lithium/kg using a plastic syringe fitted with a metal curved gavage tube. Sample K at 150 μg metal lithium/kg was delivered slowly with a pipette into the lower rectum, immediately after the anal sphincter. Mice treated in the same conditions with "empty" reverse micelles (sample 19) (12 mice per group) were used as control.

After a 4-week treatment, mice were tails suspended during 6 min and depression-like behaviour was characterized by time spent to be immobile. The total time of immobility was recorded.

Figure 11:
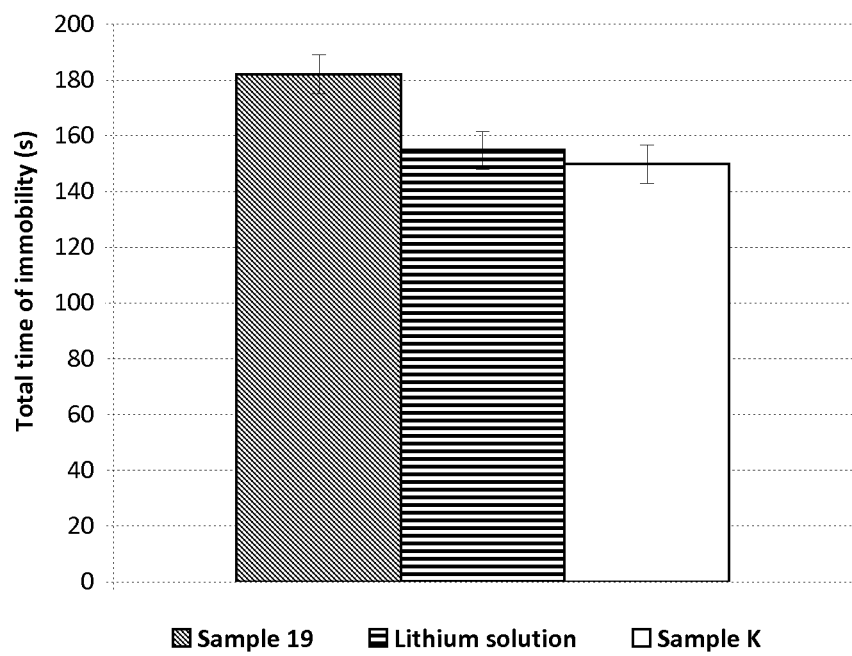
FIG. 11: In vivo evaluation of efficacy of lithium in reverse micelles on mice behavioural model of depression (tail suspension test).

Results of tail suspension test are shown in FIG. 11 which clearly demonstrates that times of immobility of mice treated with lithium in solution at 16 mg/kg or formulated in reverse micelles at 150 μg/kg (sample K) are significantly lower than the time of immobility of mice treated with reverse micelles containing no metal (sample 19).

This experiment shows that, the depression-like behaviour induced by tail suspension test is alleviated by both lithium treatment. Furthermore, the formulation of lithium in reverse micelles according to the invention affords a dose decrease by 100 times compared to the dose of lithium in solution.

Example 11

Formulation of Reverse Micelles with High Concentration of Lithium

The aim of this study was to formulate lithium in reverse micelles at 1200 μg/ml according to the invention.

Sample L: 569.9 g of lecithin were dissolved in 342.1 g of absolute ethanol by magnetic stirring at 100 r/min for 15 minutes at room temperature. 95.2 g of phytosterol were added to the mixture and stirred in the same conditions. 2313.4 g of glycerol monooleate were added thereto and magnetic stirring was carried out at 200 r/min for 120 minutes at 37° C. 480.0 g of purified water containing 6478.1 mg of lithium citrate (480.0 mg of metal lithium) were added to this oil mixture and stirred at room temperature at 200 r/min for 15 minutes to form reverse micelles containing 1200 μg metal lithium/ml (density of 0.95).

The formation of thermodynamically stable microemulsion according to the procedure above was evaluated by the visual determination of its limpidity.

This experiment shows that the addition of lecithin at 15% allows the formation of a limpid thermodynamically stable microemulsion with 1200 μg/ml of metal lithium.

The invention claimed is:

1. A reverse micelle system comprising 150-1500 μg/ml of at least one metal ion, a sterol, an acylglycerol, lecithin, an alcohol and water, wherein the weight ratio of lecithin to acylglycerol is from 0.05 to 0.40.

2. The reverse micelle system according to claim 1, wherein the micelles have aqueous cores of: a) 4 nm; b) from 3 to 5 nm; c) from 3.5 to 5 nm; or d) from 3.7 to 4.5 nm.

3. The reverse micelle system according to claim 1, obtainable by the following method:
   (a) contacting (i) a sterol, (ii) an acylglycerol, (iii) lecithin, (iv) an alcohol, (v) water, and (vi) at least one metal ion, and
   (b) stirring the mixture obtained in (a) at 40° C. or less for a time sufficient to obtain formation of reverse micelles.

4. The reverse micelle system according to claim 1, wherein the weight ratio of sterol/acylglycerol ranges from 0.015 to 0.05 or from 0.03 to 0.04.

5. The reverse micelle system according to claim 3, wherein the stirring of step (b) is carried out at a temperature ranging from 15° C. to 40° C., from 25° C. to 40° C., or from 30° C. to 37° C.

6. The reverse micelle system according to claim 1, wherein the acylglycerol is selected from the group consisting of 1,2-diolein and 1-oleoyl-2-acetyl glycerol.

7. The reverse micelle system according to claim 1, wherein the sterol is sitosterol or cholesterol.

8. The reverse micelle system according to claim 1, wherein the metal ion is selected from the group consisting of lithium, zinc, niobium, vanadium, selenium, molybdenum, chromium, antimony, tin, gold, ruthenium, palladium, platinum, strontium, arsenic, manganese and mixtures thereof.

9. A pharmaceutical composition comprising a reverse micelle system according to claim 1 and at least a pharmaceutically acceptable carrier, excipient or support.

10. The pharmaceutical composition according to claim 9, wherein the metal ion is lithium.

11. The pharmaceutical composition according to claim 9, wherein the metal ion is vanadium.

12. The pharmaceutical composition according to claim 9, wherein the metal ion is strontium.

13. The pharmaceutical composition according to claim 9, wherein the metal ion is manganese.

14. The pharmaceutical composition according to claim 9, wherein the metal ions in the reverse micelle system cross the blood brain barrier.

15. A method for the delivery of at least one metal ion to a mammal, wherein said method comprises mucosal administration to said mammal of the pharmaceutical composition according to claim 9.

16. A method for the treatment or improvement of the symptoms of a disease or disorder selected from pathologies of the central nervous system (CNS), neurodegenerative diseases, autoimmune diseases, type 2 diabetes, insulin resistance, metabolic syndrome, cancers, respiratory tumors, acute promyelocytic leukemia, acquired immunodeficiency syndromes, osteoporosis, diseases linked to oxidative stress, bipolar disorders, depression, and inflammatory disorders, wherein said method comprises administration to a mammal in need of such treatment and/or improvement of the pharmaceutical composition according to claim 9.

17. The method according to claim 16, wherein the disease or disorder is selected from pathologies of the CNS and neurodegenerative diseases.

18. The method according to claim 16, wherein the disease or disorder is selected from type 2 diabetes, insulin resistance and metabolic syndrome.

19. The method according to claim 16, wherein the disease or disorder is osteoporosis.

20. The method according to claim 16, wherein the disease or disorder is selected from disorders linked to oxidative stress.

21. The method according to claim 16, wherein the disease or disorder is selected from genetic, tumoral, viral and degenerative diseases in the central nervous system.

22. The reverse micelle system according to claim 8, wherein the metal ion is arsenic.

23. The reverse micelle system according to claim 1, said reverse micelle system consisting of 150-1500 μg/ml of at least one metal ion, a sterol, an acylglycerol, lecithin, an alcohol and water, wherein the weight ratio of lecithin to acylglycerol is from 0.05 to 0.40.

24. The reverse micelle system according to claim 1, wherein the water is present in an amount, by weight, ranging from 5 g to 15 g per 100 ml total volume of said system.

25. The reverse micelle system according to claim 1, wherein the alcohol is present in an amount, by weight, ranging from 5 g to 12 g per 100 ml total volume of said system.

26. The reverse micelle system according to claim 1, wherein the water is present in an amount, by weight, ranging from 5 g to 15 g per 100 ml total volume of said system and the alcohol is present in an amount, by weight, ranging from 5 g to 12 g per 100 ml total volume of said system.

27. The reverse micelle system of claim 1, wherein the system comprises 180 μg/ml of at least one metal ion.

28. The reverse micelle system of claim 1, wherein the system comprises 300 μg/ml of at least one metal ion.

29. The reverse micelle system of claim 1, wherein the system comprises 600 μg/ml of at least one metal ion.

30. The pharmaceutical composition according to claim 10, wherein the composition comprises 150-1200 μg/ml of lithium.

31. The pharmaceutical composition according to claim 30, wherein the composition comprises 600 μg/ml of lithium.

32. The reverse micelle system of claim 1, wherein the acylglycerol has the following formula (I):

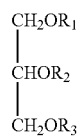

in which:
- $R_1$ is an acyl residue of a linear or branched, saturated or unsaturated fatty acid having between 14 and 24 carbon atoms, a hydrogen atom, or a mono-, di- or tri-galactose or glucose;
- $R_2$ is an acyl residue of a linear or branched, saturated or unsaturated fatty acid having between 2 and 18 carbon atoms; and
- $R_3$ is an acyl residue of a linear or branched, saturated or unsaturated fatty acid having between 14 and 24 carbon atoms, or a hydrogen atom.

33. The reverse micelle system of claim 1, wherein the acylglycerol has the following formula (I):

in which:
- $R_1$ is an acyl residue of a linear or branched, saturated or unsaturated fatty acid having between 14 and 24 carbon atoms or a hydrogen atom;
- $R_2$ is an acyl residue of a linear or branched, saturated or unsaturated fatty acid having between 2 and 18 carbon atoms; and
- $R_3$ is a hydrogen atom.

* * * * *